United States Patent
Hirano et al.

[11] Patent Number: 5,820,878
[45] Date of Patent: Oct. 13, 1998

[54] PERCUTANEOUSLY ABSORBABLE PATCH

[75] Inventors: Munehiko Hirano; Miyuki Shinmura; Masaki Kojima, all of Tsukuba, Japan

[73] Assignee: Hisamitsu Pharmaceutical Co., Inc., Tosu, Japan

[21] Appl. No.: 817,878
[22] PCT Filed: Nov. 15, 1995
[86] PCT No.: PCT/JP95/02336
§ 371 Date: Apr. 28, 1997
§ 102(e) Date: Apr. 28, 1997
[87] PCT Pub. No.: WO96/15776
PCT Pub. Date: May 30, 1996

[30] Foreign Application Priority Data

Nov. 18, 1994 [JP] Japan ................................. 6-309762

[51] Int. Cl.$^6$ .......................... A61F 13/02; A61L 15/16
[52] U.S. Cl. ........................................ 424/449; 424/448
[58] Field of Search ..................................... 424/448, 449

[56] References Cited

FOREIGN PATENT DOCUMENTS 3-116015  5/1991  Japan.
3-116731  11/1992  Japan.

*Primary Examiner*—Thurman K. Page
*Assistant Examiner*—Kathryne E. Shelborne
*Attorney, Agent, or Firm*—Kubovcik & Kubovcik

[57] ABSTRACT

A percutaneously absorbable preparation-containing patch, wherein the preparation comprises: (1) a base comprising as essential ingredients a (A–B) n–A based elastomer wherein A is substantially a monovinyl-substituted aromatic compound polymer block, B is substantially a conjugated diolefin copolymer block, and n is an integer of 3–7, crotamiton, and a softening agent; and (2) at least two hormones, especially estrogen and luteal hormones, as active ingredients.

7 Claims, 3 Drawing Sheets

PERCUTANEOUSLY ABSORBABLE PATCH

This application is a 35USC371 of PCT/JP95/02336 filed Nov. 15, 1995.

TECHNICAL FIELD

This invention relates to a percutaneously absorbable preparation-containing patch suitable for persistently releasing estrogen and luteal hormone as medicinal ingredients from the preparation.

BACKGROUND ART

Estradiol contained in estrogen is secreted from the ovary of a woman during her reproducible period of time. Thus, women who are at the menopause or thereabouts become lacking in estradiol whereupon they suffer from their menopausal disorder, irregular menstruation or the like. Remedies for these symptoms are now taken by the use of orally administrable preparations, but these preparations are rapidly metabolized by digestive canals such as stomachs and intestines and also by livers to be made inactive. Thus, in order to obtain sufficient medicinal efficacy, a large dose of estradiol must be administered. The use of such a high dose is very likely to cause adverse side effects and the like.

Accordingly, the use of estradiol in combination with luteal hormone, which, through percutaneous administration, can reduce the metabolism of estradiol and permits the estradiol to reach blood and, at the same time, inhibits the side effects of the estradiol per se, has been studied in the art.

For example, Japanese Pat. Appln. Laid-Open Gazette No. 342532/92 discloses a percutaneously absorbable preparation which comprises estradiol and luteal hormones as active ingredients and a tackifier composed mainly of an acrylic tackifier consisting of 2-ethylhexyl acrylate and N-vinyl-2-pyrrolidone. The acrylic tackifier, however, has poor capability of releasing drugs and has strong irritation to the skin, thereby rendering said preparation unsuitable for continuous administration for a long period of time. Japanese Patent Gazette No. 51623/94 discloses a method wherein estradiol and norethisterone acetate as active ingredients are dissolved in a gel comprising hydroxypropyl cellulose and ethanol, this is then formed to a reservoir type, and the release of the active ingredients is regulated with the aid of a permeant regulating membrane. Ethanol, however, has strong irritation to the skin and causes side effects such as rubefaction at preparation-applied sites very frequently.

The percutaneously absorbable patches containing a preparation under various studies as mentioned above are low in biological utility since the active ingredients contained therein can be used only to a limited extent. In addition, the tackifier per se or the addition of absorption accelerators such as ethanol will raise a problem of skin irritation since the preparation is attempted to be percutaneously administered.

SUMMARY OF THE INVENTION

In view of the above disadvantages, the inventors of this invention have made intensive studies with a view to providing percutaneously absorbable patch containing a preparation, which has 1) a simple structure,
2) improved biological utility, and
3) reduced skin irritation thus completing this invention.

Thus, the percutaneously absorbable preparation-containing patch of this invention comprises: (1) a base comprising as essential ingredients a (A–B) n–A based elastomer (elastic polymer) (wherein A is substantially a monovinyl-substituted aromatic compound polymer block, B is substantially a conjugated diolefin copolymer block and n is an integer of 3–7), crotamiton and a softening agent; and (2) at least two hormones as active ingredients.

According to this invention, at least two hormones are contained as the active ingredients. Estrogen and luteal hormone are usually used as the two active ingredients.

Examples of the estrogen are estradiol, estrone, estriol, equilin, equilenin and derivatives thereof. Among them, estradiol is usually used in the percutaneously absorbable preparation contained in the patch according to this invention.

The luteal hormone is suitably selected from the group consisting of progesterone, hydroxyprogesterone caproate, medroxyprogesterone acetate, dydrogesterone, chlormadinone acetate, ethisterone, dimethisterone, norethisterone, norethisterone acetate, norethisterone enanthate, ethynodial acetate, megestrol acetate and allylestrenol.

The content of the estrogen exemplified by the estradiol is 0.01 to 10% by weight, preferably 0.05 to 5% by weight, more preferably 0.1 to 1% by weight, based on the total amount of the pharmaceutical preparation. Although the content of the luteal hormone varies depending upon the kind thereof, it is usually 0.01 to 10% by weight, preferably 0.05 to 5% by weight, more preferably 0.1 to 1% by weight, based on the total amount of the pharmaceutical preparation. The content of the luteal hormone is preferably 1 to 5 times (weight ratio) that of estrogen exemplified by estradiol.

In this invention, the (A–B) n–A based elastomers usable as the base are those which are commercially easily available and include a styrene-butadiene-styrene block copolymer (trade name: Califlex TR-1101 produced by Shell Chemical Corp.), a styrene-isoprene-styrene block copolymer (trade name: Califlex TR-1107 and Califlex TR-1111 produced by Shell Chemical Corp.), a styrene-isoprene-styrene block copolymer (trade name: JSR 5000 and JSR 5100 produced by Nippon Synthetic Rubber Co.) and a styrene-isoprene-styrene block copolymer (trade name: Quintack 3421 produced by Nippon Zeon Co.) with the styrene-isoprene-styrene block copolymer being particularly preferred. The use of the (A–B) n–A type elastomers as the base for the preparations will greatly enhance the releasability of the estrogen exemplified by estradiol and the luteal hormone as well as the biological utilizability thereof.

Crotamiton used in this invention markedly improves the preparations in solubility of both the estrogen exemplified by estradiol and the luteal hormone contained in the preparations, in releasability of these active ingredients from the preparations, and in percutaneous absorption of these active ingredients and the like. Further, crotamiton has never been incorporated as a solubilizer and absorption accelerator for the estrogen (exemplified by estradiol) and the luteal hormone into the (A–B) n–A based elastomer supported preparation before the accomplishment of this invention and there is found no literature which suggests such incorporation of crotamiton as mentioned above.

Examples of softening agents used in this invention include liquid paraffin, polybutene, castor oil, cotton seed oil, palm oil, coconut oil, and process oil.

The use of the base containing as the essential components the (A–B) n–A type elastomer, the crotamiton, and the softening agent will enhance the biological utilizability of said hormones and will reduce rubefaction and rash which are otherwise caused by medicinal irritation to the skin.

The preferable contents of the (A–B) n–A based elastic polymer, the crotamiton, and the softening agent in the percutaneously absorbable preparation contained in the patch according to this invention are as follows.

The total content of the essential ingredients consisting of the (A–B) n–A based elastomer and the crotamiton, is preferably 20 to 99% by weight, more preferably 30 to 60% by weight based on the total amount of the preparation. For the content of each ingredient, the content of the (A–B) n–A based elastomer is preferably 5 to 50% by weight, more preferably 10 to 20% by weight, based on the total amount of the preparation, the content of the crotamiton is preferably 1–20% by weight, more preferably 3 to 10% by weight, based on the total amount of the preparation, and the content of the softening agent is preferably 10 to 70% by weight, more preferably 20 to 65% by weight, based on the total amount of the preparation. The combination of the ingredients having the above respective contents is best for attaining the effect of this invention.

The percutaneously absorbable preparation contained in the patch of this invention may contain conventional additives in addition to the above essential ingredients. Specific examples of the conventional additives are synthetic rubbers, such as polyisobutyrene; tackifiers, such as saturated alicyclic hydrocarbon resins (for example, Arcon P-100 (trade name)), rosin esters (for example, KE-311 (trade name), KE-100 (trade name), or Super Ester S-100 (trade name)), alicyclic hydrocarbons (for example, Escorez 5300 (trade name)), terpene hydrogenated resins (for example, Clearon P-105 (trade name)), and hydrogenated rosin esters (for example, Foral 105 (trade name)); and super absorbent polymers, such as Sumikagel SP-520 (trade name), Aquakeep 4SH (trade name), Arasorb 800F (trade name), Sunwet 1M-300MPS (trade name), and Sunwet 1M-1000MPS (trade name), and inorganic fillers, such as zinc calcium carbonate, titanium dioxide, and silica. They may be added in a suitable amount.

The content of the tackifier is 0 to 40% by weight based on the total amount of the preparation and, when the maintenance of satisfactory tackiness is required, is 5 to 40% by weight based on the total amount of the preparation. Although the above content suffices for attaining the purposes, it is more preferably 10 to 30% by weight. The content of the water-absorptive polymer is 0 to 15% by weight based on the total amount of the preparation and, when optionally added to the preparation, is preferably 0.1 to 10% by weight, more preferably 0.5 to 5% by weight.

The support for the preparation of this invention is preferably one having no influence on the release of the drug and, in addition, superior flexibility and is preferably selected from a film or woven fabric of polyester, polypropylene, polyethylene or the like and an aluminum foil, or a flexible composite material comprising a laminate of these plastic films or woven fabrics.

The dosage form of the percutaneously absorbable preparation contained in the patch of this invention is preferably a plaster, particularly preferably an anhydrous plaster.

A general process for producing the percutaneously absorbable preparation-containing patch of this invention will be described hereunder. All ingredients of a base except for crotamiton are heat melted and then incorporated with active ingredients and crotamiton to obtain a preparation which is then spread over a support, covered with a liner and then cut into a desired shape to produce preparation-containing patches. Alternatively, the preparation may be once applied over a film which has been treated to be made releasable, after which the preparation-applied film was pressed against a suitable support to transfer the spread preparation thereto, and suitably cut thereby producing preparation-containing patches. Further, it is also possible to use a method which comprises dissolving all the ingredients in an organic solvent such as hexane, toluene or ethyl acetate, spreading the solution on a support, removing the organic solvent to produce a preparation, covering the preparation with a liner and then cutting the preparation-coated support into a predetermined shape to produce preparation-coated patches, or a method which comprises once spreading the above solution over a film which has been treated to be made releasable, removing the organic solvent, transferring the resulting preparation to a suitable support by pressing it against the support thereby to produce preparation-attached patches.

The percutaneously absorbable preparation-attached patches of this invention thus prepared can enhance the release of the estrogen exemplified by estradiol and the luteal hormone as active ingredients, improve the biological utilizability of these active ingredients and, at the same time, have the effect of markedly relieving the skin irritation in case of continuous administration and long-term administration.

PREFERRED EMBODIMENTS OF THE INVENTION

Figure 1:
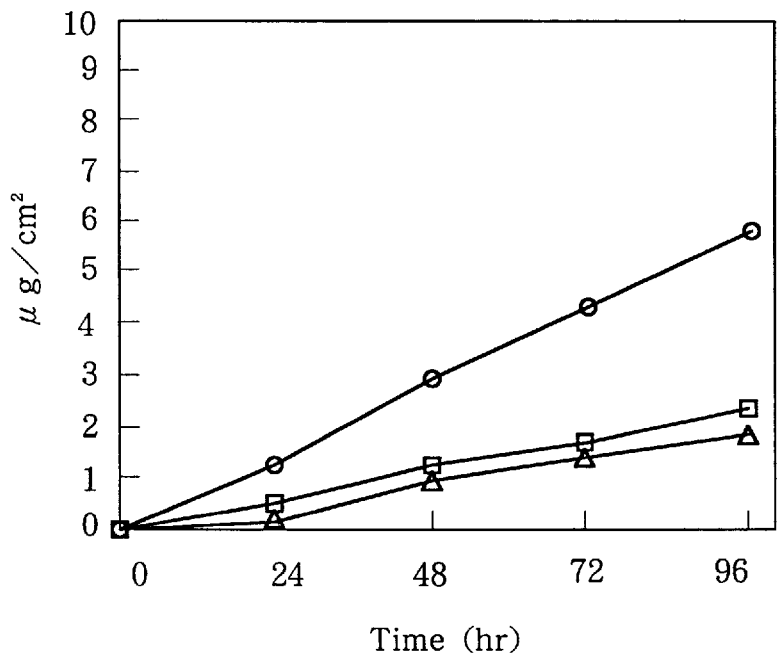
FIG. 1 shows data on estradiol in a percutaneous permeation test 1 on hairless mice. In the same Fig., the abscissa represents the preparation-applied time (hr), the ordinate the amount of the percutaneous permeation ($\mu g/cm^2$), ○ data on estradiol of Example 2, □ data on estradiol of Reference Example 1 and Δ data on estradiol of Reference Example 2.

This invention will be described in more detail referring to the following Examples, Test Examples and the like. In Examples, Comparative Examples and Reference Examples, all the numerical values are in % by weight.

Example 1

| | |
|---|---|
| Styrene-isoprene-styrene block copolymer (trade name: Califlex TR-1107) | 37.00 |
| Liquid paraffin | 61.78 |
| Butylhydroxytoluene | 0.20 |
| Crotamiton | 1.00 |
| Estradiol | 0.01 |
| Norethisterone acetate | 0.01 |

Using the above ingredients, a preparation was prepared, spread on a support and cut into a desired size, in accordance with the above general production process to produce a patch containing a percutaneously absorbable preparation of a estradiol/norethisterone acetate mixture type.

Example 2

| | |
|---|---|
| Styrene-isoprene-styrene block copolymer (Trade name: Califlex TR-1107) | 35.00 |
| Liquid paraffin | 57.00 |
| Crotamiton | 5.00 |
| Estradiol | 0.50 |
| Norethisterone acetate | 2.50 |

The procedure of Example 1 was followed except that the above ingredients were used, thereby to produce a patch containing a percutaneously absorbable preparation of an estradiol/norethisterone acetate mixture type.

Example 3

| | |
|---|---|
| Styrene-isoprene-styrene block copolymer (Trade name: Califlex TR-1107) | 28.00 |
| Liquid paraffin | 27.00 |
| Crotamiton | 20.00 |
| Super absorbent polymer (Trade name: Sumikagel SP-520) | 5.00 |
| Estradiol | 10.00 |
| Norethisterone acetate | 10.00 |

The procedure of Example 1 was followed except that the above ingredients were used, thereby to produce a patch containing a percutaneously absorbable preparation of an estradiol/norethisterone acetate mixture type.

Example 4

| | |
|---|---|
| Styrene-isoprene-styrene block copolymer (Trade name: Califlex TR-1111) | 35.00 |
| Liquid paraffin | 56.00 |
| Crotamiton | 5.00 |
| Super absorbent polymer (Trade name: Aquakeep 4SH) | 1.00 |
| Estradiol | 0.50 |
| Norethisterone | 2.50 |

The procedure of Example 1 was followed except that the above ingredients were used, thereby to produce a patch containing a percutaneously absorbable preparation of an estradiol/norethisterone mixture type.

Example 5

| | |
|---|---|
| Styrene-isoprene-styrene block copolymer (Trade name: Califlex TR-1111) | 20.00 |
| Liquid paraffin | 53.00 |
| Crotamiton | 3.00 |
| Super absorbent polymer (Trade name: Aquakeep 4SH) | 20.00 |
| Estradiol | 1.00 |
| Norethisterone | 3.00 |

The procedure of Example 1 was followed except that the above ingredients were used, thereby to produce a patch containing a percutaneously absorbable preparation of an estradiol/norethisterone mixture type.

Example 6

| | |
|---|---|
| Styrene-isoprene-styrene block copolymer (Trade name: Califlex TR-1107) | 35.00 |
| Liquid paraffin | 52.00 |
| Crotamiton | 5.00 |
| Super absorbent polymer (Trade name: Arasorb 800F) | 5.00 |
| Estradiol | 0.50 |
| Norethisterone | 2.50 |

The procedure of Example 1 was followed except that the above ingredients were used, thereby to produce a patch containing a percutaneously absorbable preparation of an estradiol/norethisterone mixture type.

Example 7

| | |
|---|---|
| Styrene-isoprene-styrene block copolymer (Trade name: Califlex TR-1111) | 35.00 |
| Liquid paraffin | 52.00 |
| Crotamiton | 4.00 |
| Super absorbent polymer (Trade name: Arasorb S-100F) | 5.00 |
| Estradiol | 1.00 |
| Norethisterone | 3.00 |

The procedure of Example 1 was followed except that the above ingredients were used, thereby to produce a patch containing a percutaneously absorbable preparation of an estradiol/norethisterone mixture type.

Example 8

| | |
|---|---|
| Styrene-isoprene-styrene block copolymer (Trade name: Califlex TR-1111) | 35.00 |
| Liquid paraffin | 53.00 |
| Crotamiton | 5.00 |
| Super absorbent polymer (Trade name: Sunwet IM-300MPS) | 5.00 |
| Estradiol | 0.50 |
| Medroxyprogesterone acetate | 1.50 |

The procedure of Example 1 was followed except that the above ingredients were used, thereby to produce a patch containing a percutaneously absorbable preparation of an estradiol/medroxyprogesterone acetate mixture type.

Example 9

| | |
|---|---:|
| Styrene-isoprene-styrene block copolymer (Trade name: Califlex TR-1111) | 35.00 |
| Liquid paraffin | 53.00 |
| Crotamiton | 5.00 |
| Super absorbent polymer (Trade name: Sunwet IM-1000MPS) | 5.00 |
| Estradiol | 0.50 |
| Medroxyprogesterone acetate | 1.50 |

The procedure of Example 1 was followed except that the above ingredients were used, thereby to produce a patch containing a percutaneously absorbable preparation of an estradiol/medroxyprogesterone acetate mixture type.

Example 10

| | |
|---|---:|
| Styrene-isoprene-styrene block copolymer (Trade name: Califlex TR-1111) | 40.00 |
| Polyisobutylene | 5.00 |
| Liquid paraffin | 37.70 |
| Butylhydroxytoluene | 0.30 |
| Crotamiton | 5.00 |
| Tackifier (alicyclic saturated hydrocarbon resin) (Trade name: Arcon F-100) | 10.00 |
| Estradiol | 0.50 |
| Medroxyprogesterone acetate | 1.50 |

The procedure of Example 1 was followed except that the above ingredients were used, thereby to produce a patch containing a percutaneously absorbable preparation of an estradiol/medroxyprogesterone acetate mixture type.

Example 11

| | |
|---|---:|
| Styrene-isoprene-styrene block copolymer (Trade name: Califlex TR-1107) | 5.00 |
| Polyisobutylene | 10.00 |
| Liquid paraffin | 40.00 |
| Crotamiton | 6.00 |
| Tackifier (alicyclic saturated hydrocarbon resin) (Trade name: Arcon P-100) | 35.00 |
| Estradiol | 1.00 |
| Medroxyprogesterone acetate | 3.00 |

The procedure of Example 1 was followed except that the above ingredients were used, thereby to produce a patch containing a percutaneously absorbable preparation of an estradiol/medroxyprogesterone acetate mixture type.

Example 12

| | |
|---|---:|
| Styrene-isoprene-styrene block copolymer (Trade name: Califlex TR-1107) | 50.00 |
| Liquid paraffin | 26.00 |
| Butylhydroxytoluene | 0.50 |
| Crotamiton | 5.00 |
| Super absorbent polymer (Trade name: Arasorb S-100F) | 2.00 |
| Tackifier (alicyclic saturated hydrocarbon resin) (Trade name: Arcon P-100) | 12.50 |
| Estradiol | 1.00 |
| Progesterone | 3.00 |

The procedure of Example 1 was followed except that the above ingredients were used, thereby to produce a patch containing a percutaneously absorbable preparation of an estradiol/progesterone mixture type.

Example 13

| | |
|---|---:|
| Styrene-isoprene-styrene block copolymer (Trade name: Califlex TR-1111) | 27.00 |
| Liquid paraffin | 41.00 |
| Crotamiton | 3.00 |
| Tackifier (rosin ester) (Trade name: KE-311) | 25.00 |
| Estradiol | 1.00 |
| Progesterone | 3.00 |

The procedure of Example 1 was followed except that the above ingredients were used, thereby to produce a patch containing a percutaneously absorbable preparation of an estradiol/progesterone mixture type.

Example 14

| | |
|---|---:|
| Styrene-isoprene-styrene block copolymer (Trade name: Califlex TR-1111) | 50.00 |
| Polyisobutylene | 2.00 |
| Liquid paraffin | 30.80 |
| Butylhydroxytoluene | 0.20 |
| Crotamiton | 5.00 |
| Tackifier (hydrogenated alicyclic hydrocarbon) (Trade name: Escorez 5300) | 10.00 |
| Estradiol | 0.50 |
| Progesterone | 1.50 |

The procedure of Example 1 was followed except that the above ingredients were used, thereby to produce a patch containing a percutaneously absorbable preparation of an estradiol/progesterone mixture type.

Example 15

| | |
|---|---:|
| Styrene-isoprene-styrene block copolymer (Trade name: Califlex TR-1111) | 20.00 |
| Liquid paraffin | 33.00 |
| Crotamiton | 5.00 |
| Tackifier (alicyclic saturated hydrocarbon resin) (Trade name: P-100) | 36.00 |
| Estradiol | 1.00 |
| Norethisterone acetate | 5.00 |

The procedure of Example 1 was followed except that the above ingredients were used, thereby to produce a patch containing a percutaneously absorbable preparation of an estradiol/norethisterone acetate mixture type.

Example 16

| | |
|---|---:|
| Styrene-isoprene-styrene block copolymer (Trade name: Califlex TR-1111) | 29.50 |
| Liquid paraffin | 30.00 |
| Crotamiton | 7.50 |
| Super absorbent polymer (Trade name: Sunwet IM-1000MPS) | 10.00 |
| Tackifier (hydrogenated alicyclic hydrocarbon) (Trade name: Escorez 5300) | 20.00 |
| Estradiol | 0.50 |
| Norethisterone acetate | 2.50 |

The procedure of Example 1 was followed except that the above ingredients were used, thereby to produce a patch containing a percutaneously absorbable preparation of an estradiol/norethisterone acetate mixture type.

Example 17

| | |
|---|---|
| Styrene-isoprene-styrene block copolymer (Trade name: Califlex TR-1107) | 22.50 |
| Liquid paraffin | 39.50 |
| Crotamiton | 10.00 |
| Tackifier (alicyclic saturated hydrocarbon resin) (Trade name: P-100) | 25.00 |
| Estradiol | 0.50 |
| Norethisterone acetate | 2.50 |

The procedure of Example 1 was followed except that the above ingredients were used, thereby to produce a patch containing a percutaneously absorbable preparation of an estradiol/norethisterone acetate mixture type.

Example 18

| | |
|---|---|
| Styrene-isoprene-styrene block copolymer (Trade name: Califlex TR-1111) | 5.00 |
| Liquid paraffin | 60.00 |
| Crotamiton | 3.00 |
| Tackifier (rosin ester) (Trade name: Super Ester S-100) | 30.00 |
| Estradiol | 1.00 |
| Norethisterone | 1.00 |

The procedure of Example 1 was followed except that the above ingredients were used, thereby to produce a patch containing a percutaneously absorbable preparation of an estradiol/norethisterone mixture type.

Example 19

| | |
|---|---|
| Styrene-isoprene-styrene block copolymer (Trade name: Califlex TR-1111) | 27.00 |
| Liquid paraffin | 40.00 |
| Crotamiton | 5.00 |
| Tackifier (alicyclic saturated hydrocarbon resin) (Trade name: Arcon P-100) | 25.00 |
| Estradiol | 1.00 |
| Norethisterone | 2.00 |

The procedure of Example 1 was followed except that the above ingredients were used, thereby to produce a patch containing a percutaneously absorbable preparation of an estradiol/norethisterone mixture type.

Example 20

| | |
|---|---|
| Styrene-isoprene-styrene block copolymer (Trade name: Califlex TR-1107) | 34.50 |
| Liquid paraffin | 42.50 |
| Crotamiton | 5.00 |
| Tackifier (hydrogenated rosin ester) (Trade name: Foral 105) | 15.00 |
| Estradiol | 0.50 |
| Medroxyprogesterone acetate | 2.50 |

The procedure of Example 1 was followed except that the above ingredients were used, thereby to produce a patch containing a percutaneously absorbable preparation of an estradiol/medroxyprogesterone acetate mixture type.

Example 21

| | |
|---|---|
| Styrene-isoprene-styrene block copolymer (Trade name: Califlex TR-1111) | 34.50 |
| Liquid paraffin | 34.00 |
| Polyisobutylene | 8.00 |
| Crotamiton | 3.00 |
| Super absorbent polymer (Trade name: Arasorb 800F) | 3.00 |
| Tackifier (terpene hydrogenated resin) (Trade name: Clearon P-105) | 15.00 |
| Estradiol | 0.50 |
| Medroxyprogesterone acetate | 2.00 |

The procedure of Example 1 was followed except that the above ingredients were used, thereby to produce a patch containing a percutaneously absorbable preparation of an estradiol/medroxyprogesterone acetate mixture type.

Example 22

| | |
|---|---|
| Styrene-isoprene-styrene block copolymer (Trade name: Califlex TR-1111) | 25.00 |
| Liquid paraffin | 40.00 |
| Crotamiton | 4.00 |
| Tackifier (hydrogenated alicyclic hydrocarbon resin) (Trade name: Escorez 5300) | 25.00 |
| Estradiol | 1.00 |
| Progesterone | 5.00 |

The procedure of Example 1 was followed except that the above ingredients were used, thereby to produce a patch containing a percutaneously absorbable preparation of an estradiol/progesterone mixture type.

Example 23

| | |
|---|---|
| Styrene-isoprene-styrene block copolymer (Trade name: Califlex TR-1107) | 22.50 |
| Polyisobutylene | 5.00 |
| Liquid paraffin | 36.50 |
| Crotamiton | 5.00 |
| Super absorbent polymer (Trade name: Arasorb S-100F) | 3.00 |
| Tackifier (rosin ester) (Trade name: KE-311) | 25.00 |
| Estradiol | 0.50 |
| Norethisterone acetate | 2.50 |

The procedure of Example 1 was followed except that the above ingredients were used, thereby to produce a patch containing a percutaneously absorbable preparation of an estradiol/norethisterone acetate mixture type.

Example 24

| | |
|---|---|
| Styrene-isoprene-styrene block copolymer (Trade name: Califlex TR-1111) | 34.50 |
| Liquid paraffin | 40.50 |
| Crotamiton | 3.00 |
| Super absorbent polymer (Trade name: Arasorb S-100F) | 3.00 |
| Tackifier (rosin ester) (Trade name: KE-311) | 15.00 |
| Estradiol | 1.00 |
| Norethisterone acetate | 3.00 |

The procedure of Example 1 was followed except that the above ingredients were used, thereby to produce a patch containing a percutaneously absorbable preparation of an estradiol/norethisterone acetate mixture type.

Example 25

| | |
|---|---|
| Styrene-isoprene-styrene block copolymer (Trade name: Califlex TR-1107) | 25.00 |
| Polyisobutylene | 5.00 |
| Liquid paraffin | 41.90 |
| Tackifier (rosin ester) (Trade name: KE-311) | 25.00 |
| Crotamiton | 0.10 |
| Estradiol | 0.50 |
| Norethisterone acetate | 2.50 |

The procedure of Example 1 was followed except that the above ingredients were used, thereby to produce a patch containing a percutaneously absorbable preparation of an estradiol/norethisterone acetate mixture type.

Comparative Example 1

| | |
|---|---|
| Styrene-isoprene-styrene block copolymer (Trade name: Califlex TR-1107) | 25.00 |
| Polyisobutylene | 5.00 |
| Liquid paraffin | 42.00 |
| Tackifier (rosin ester) (Trade name: KE-311) | 25.00 |
| Estradiol | 0.50 |
| Norethisterone acetate | 2.50 |

The procedure of Example 1 was followed except that the above ingredients were used, thereby to produce a patch containing a percutaneously absorbable preparation of an estradiol/norethisterone acetate mixture type.

Reference Example 1

| | |
|---|---|
| Acryl resin-based solvent-type pressure sensitive adhesive (Trade name: NISSETSU PE-300, solid content 40%) | 92.00 (solid content) |
| Crotamiton | 5.00 |
| Estradiol | 0.50 |
| Norethisterone acetate | 2.50 |

The procedure of Example 1 was followed except that the above ingredients were mixed together to form a mixture which was applied to a backing material (such as a support or liner) in such a manner that the thickness of the thus applied mixture on the backing material was the same as those in the Examples after the solvent of the former has been evaporated. The dried mixture attached to the backing material was cut into pieces of a desired size to prepare a patch containing a percutaneously absorbable preparation of a estradiol/norethisterone acetate mixture type.

Reference Example 2

| | |
|---|---|
| Silicon adhesive (Trade name: Silascon 355 Medical Adhesive, solid content 18.5%) | 92.00 (solid content) |
| Crotamiton | 5.00 |
| Estradiol | 0.50 |
| Norethisterone acetate | 2.50 |

The procedure of Reference Example 1 was followed except that the above ingredients were used, thereby to produce a patch containing a percutaneously absorbable preparation of a estradiol/norethisterone acetate mixture type.

Experiment 1
(Percutaneous permeation test 1 on hairless mice)

Figure 2:
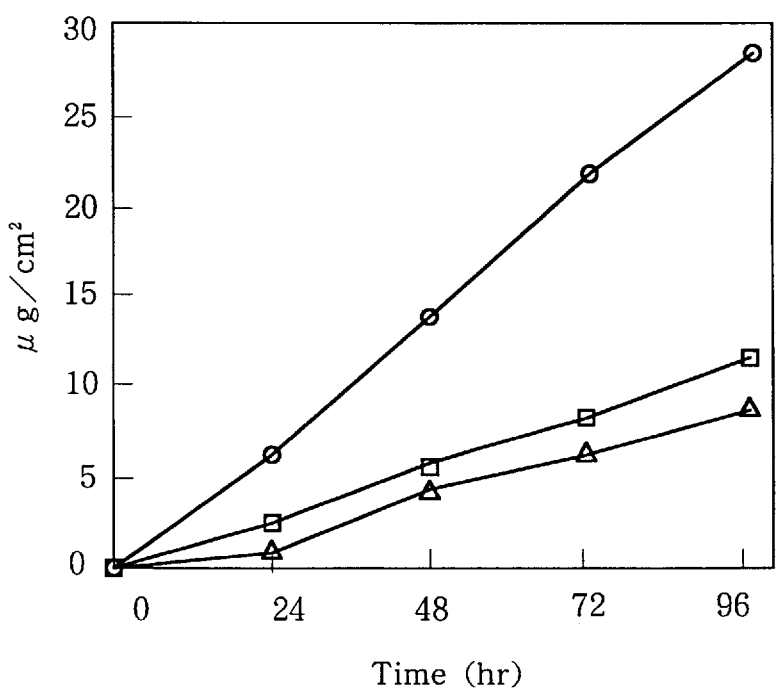
FIG. 2 shows data on norethisterone acetate in a percutaneous permeation test 1 on hairless mice. In the same Fig., the abscissa represents the preparation-applied time (hr), the ordinate the amount of the percutaneous permeation ($\mu g/cm^2$), ○ data on norethisterone acetate of Example 2, □ data on norethisterone acetate of Reference Example 1 and data on norethisterone acetate of Reference Example 2.

Percutaneous permeation tests were made on hairless mice using the patches obtained in Example 2 and Reference Examples 1–2, respectively. The results are shown in FIGS. 1 and 2. As is seen from the result, the patch of Example 2 clearly exhibits excellent release of estradiol and norethisterone acetate as compared with those of Reference Examples 1–2. This is because the preparation of the present invention contains the (A–B) n–A based elastomer, crotamiton and the softening agent as the base component.

Experiment 2
(Percutaneous permeation test 2 on hairless mice)

Figure 3:
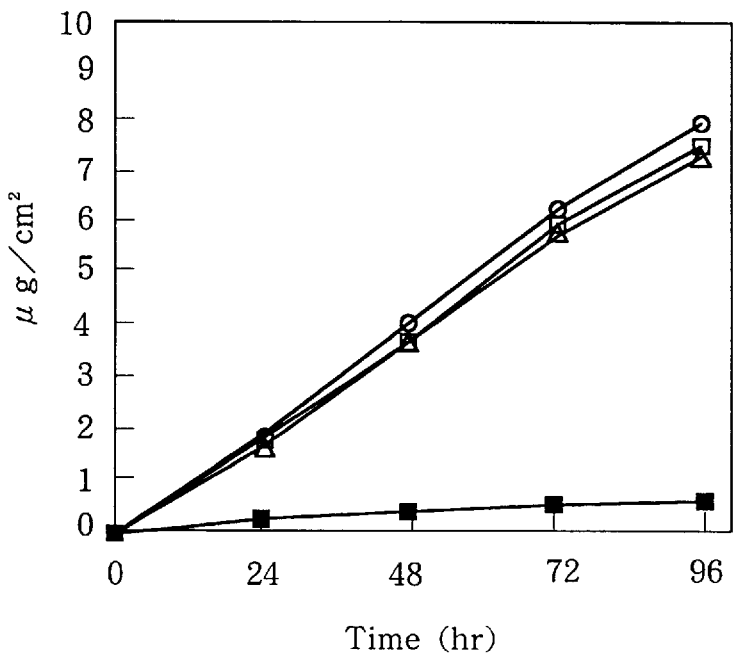
FIG. 3 shows data on estradiol in a percutaneous permeation test 2 on hairless mice. In the same Fig., the abscissa represents the preparation-applied time (hr), the ordinate the amount of the percutaneous permeation ($\mu g/cm^2$), ○ data on estradiol of Example 23, □ data on estradiol of Example 17, Δ data on estradiol of Example 15 and ■ data on estradiol of Comparative Example 1.
Figure 4:
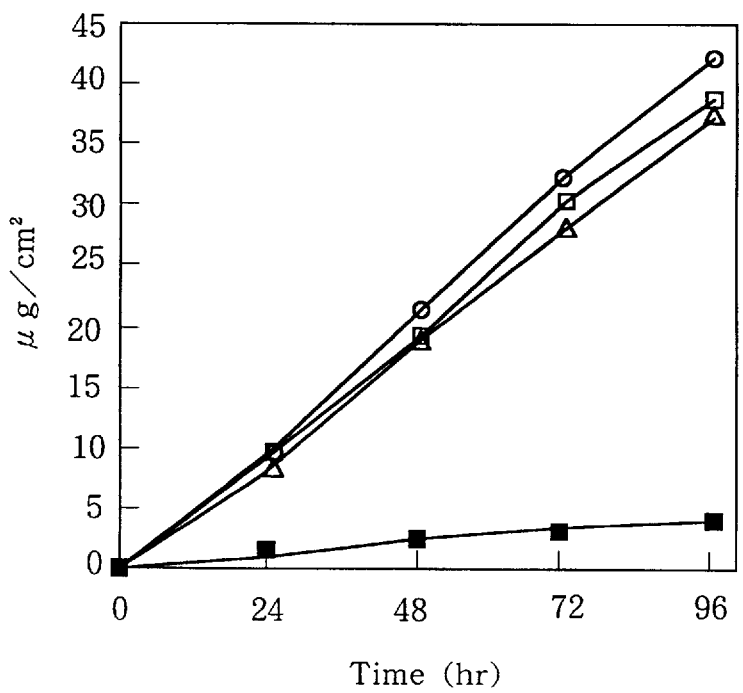
FIG. 4 shows data on norethisterone acetate in a percutaneous permeation test 2 on hairless mice. In the same Fig., the abscissa represents the preparation-applied time (hr), the ordinate the amount of the percutaneous permeation ($\mu g/cm^2$), ○ data on norethisterone acetate of Example 23, □ data on norethisterone acetate of Example 17, Δ data on norethisterone acetate of Example 15 and ■ data on norethisterone acetate of Comparative Example 1.

Using each of the patches of Examples 15, 17 and 23 as well as the patch of Comparative Example 1, a percutaneous permeation test was made on hairless mice with the results being shown in FIGS. 3 and 4.

As is shown in the result, the patches of Examples 15, 17 and 23 clearly indicate excellent release of estradiol as compared with that of Comparative Example 1. This is because the preparation of the present invention contains crotamiton.

Experiment 3
(Test for measuring the concentration of the medicinal ingredient in the blood of rabbits)

Figure 5:
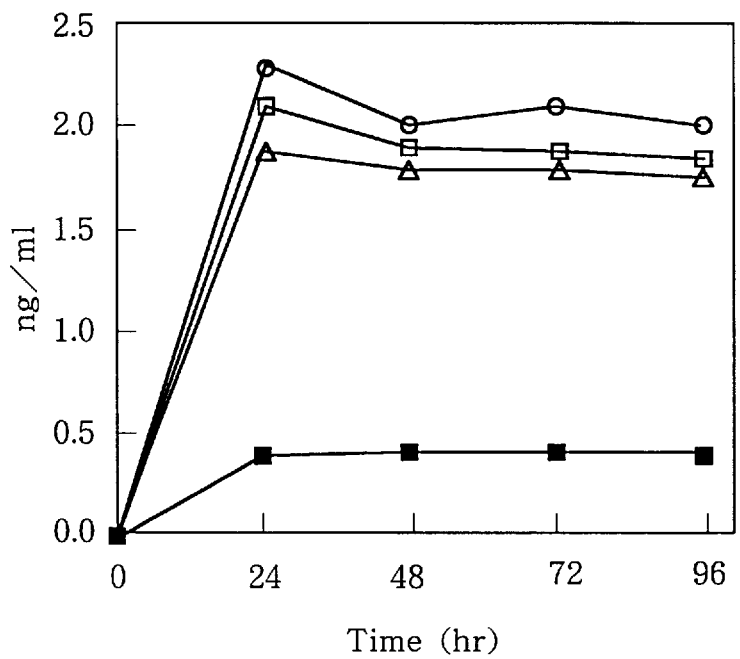
FIG. 5 shows data on estradiol in a test for measuring the active ingredients concentration in the blood of rabbits. In the same Fig., the abscissa represents the preparation applied time (hr), the ordinate the estradiol concentration in the blood (ng/ml), ○ data on estradiol of Example 23, □ data on estradiol of Example 17, Δ data on estradiol of Example 15 and ■ data on estradiol of Comparative Example 1.
Figure 6:
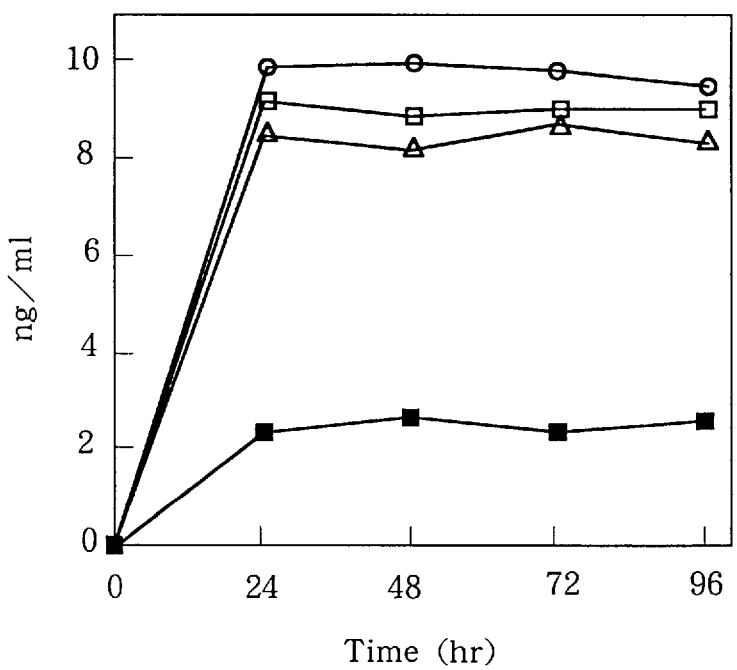
FIG. 6 shows data on norethisterone acetate in a test for measuring the active ingredients concentration in the blood of rabbits. In the same Fig., the abscissa represents the preparation-applied time (hr), the ordinate the norethisterone acetate concentration in the blood (ng/ml), ○ data on norethisterone acetate of Example 23, □ data on norethisterone acetate of Example 17, Δ date on norethisterone acetate of Example 15 and ■ data on norethisterone acetate of comparative Example 1.

Using each of the patches of Examples 15, 17 and 23 as well as the patches of Comparative Example 1, measurements for concentration of the active ingredient in the blood of rabbits were made. Nippon white-colored hares were depilated at their back and then the concentrations of estradiol and norethisterone acetate were measured with the lapse of time with the results being shown in FIGS. 5 and 6.

As is indicated in the results, the preparations of Examples 15, 17 and 23 are excellent in the rise of concentration of the medicinal ingredients in blood, the amount of the ingredients released and durability as compared with that of Comparative Example 1.

[Utilizability in the Industrial Field]

As mentioned above, the percutaneously absorbable preparation-containing patch of this invention comprising as essential ingredients the (A–B) n–A based elastomer, crotamiton and the softening agent as well as two hormones, especially an estrogen exemplified by the estradiol and a luteal hormone, as an medicinal ingredient are most suitable for release of the medicinal ingredient therefrom, exhibit sufficient medicinal efficacy without causing rubefaction, rashes and the like when used.

We claim:

1. A percutaneously absorbable preparation-containing patch, wherein the preparation comprises:

(1) 20 to 99% by weight of a base comprising as essential ingredients:

(a) 5 to 50% by weight of a $(A-B)_n-A$ based elastomer, wherein A is substantially a monovinyl-substituted aromatic compound polymer block, B is substantially a conjugated diolefin copolymer block, and n is an integer of 3–7, (b) 1 to 20% by weight of crotamiton, and (c) 10 to 70% by weight of a softening agent; and (2) 0.01 to 10% by weight of estrogen and 0.01 to 10% by weight of a luteal hormone as active ingredients, the proportion of each ingredient being based on the total amount of the pharmaceutical preparation.

2. A patch according to claim 1, wherein the preparation further contains 5 to 40% by weight of a tackifier.

3. A patch according to claim 1, wherein the preparation further contains at most 15% by weight of a super absorbent polymer.

4. A patch according to claim 1, 2 or 3, wherein the weight ratio of the content of the luteal hormone to the content of the estrogen is 1 to 5.

5. A patch according to claim 1, 2, 3 or 4, wherein the estrogen is estradiol, estrone, equilin, equilenin or a derivative thereof.

6. A patch according to claim 1, 2, 3 or 4, wherein the luteal hormone is progesterone, hydroxy-progesterone caproate, medroxyprogesterone acetate, dydrogesterone, chlormadinone acetate, ethisterone, dimethisterone, norethisterone, norethisterone acetate, norethisterone enanthate, ethynodiol acetate, megestrol acetate or allylestrenol.

7. A patch according to claim 1, 2, 3, 4, 5 or 6, wherein the preparation is in a dosage form of a plaster.

* * * * *